United States Patent [19]

Fuchs et al.

[11] Patent Number: 5,893,484

[45] Date of Patent: Apr. 13, 1999

[54] DISCHARGE DEVICE FOR FLUID MEDIA, PARTICULARLY FOR SINGLE-STROKE ONLY DISCHARGE

[75] Inventors: Karl-Heinz Fuchs, Radolfzell; Hans Merk, Gaienhofen, both of Germany

[73] Assignee: Ing. Erich Pfeiffer GmbH, Germany

[21] Appl. No.: 08/678,453

[22] Filed: Jul. 9, 1996

[30] Foreign Application Priority Data

Jul. 14, 1995 [DE] Germany ............... 195 25 734

[51] Int. Cl.$^6$ ............................................. B67D 5/00
[52] U.S. Cl. ................. 222/83; 222/321.6; 222/321.7
[58] Field of Search .................. 222/81, 82, 83, 222/321.6, 321.7

[56] References Cited

U.S. PATENT DOCUMENTS

| | | | |
|---|---|---|---|
| 2,984,570 | 5/1961 | Prell | 222/83 X |
| 3,187,749 | 6/1965 | Sarnoff | 128/218 |
| 3,367,330 | 2/1968 | Sierpin | 128/173 |
| 3,739,779 | 6/1973 | Pfleger | 128/218 DA |
| 3,917,063 | 11/1975 | Chibret et al. | 222/83 X |
| 5,289,818 | 3/1994 | Citterio et al. | 128/200.14 |
| 5,307,953 | 5/1994 | Regan | 222/82 |
| 5,409,141 | 4/1995 | Kikuchi et al. | 222/83 X |
| 5,431,155 | 7/1995 | Marelli | 128/200.14 |
| 5,511,698 | 4/1996 | Solignac | 222/162 |

FOREIGN PATENT DOCUMENTS

| | | |
|---|---|---|
| 311863 | 1/1993 | European Pat. Off. . |
| 2 667 050 A1 | 9/1990 | France . |
| 3631341 | 4/1987 | Germany . |
| 3900875 | 7/1990 | Germany . |
| 3909031 | 9/1990 | Germany . |
| 3909633 | 10/1990 | Germany . |
| 4005527 | 8/1991 | Germany . |
| 4005528 | 8/1991 | Germany . |
| 4021263 | 1/1992 | Germany . |
| 4137799 | 5/1993 | Germany . |

*Primary Examiner*—Joseph Kaufman
*Attorney, Agent, or Firm*—Quarles & Brady

[57] ABSTRACT

A disposable atomizer contains a cylindrical container for a medium to be atomized, particularly a pharmaceutical medium. The container is closed by a rubber plunger plug which has a central opening into which a closure ball is pressed. For discharging the medium, the container is pressed against an actuator which pushes the ball from the opening and thereby opens the container while, at the same time, the actuator forced down from a shoulder forms the plunger of a plunger pump formed thereby.

12 Claims, 1 Drawing Sheet

5,893,484

1

DISCHARGE DEVICE FOR FLUID MEDIA, PARTICULARLY FOR SINGLE-STROKE ONLY DISCHARGE

TECHNICAL FIELD AND BACKGROUND OF THE INVENTION

The invention relates to a discharge device for fluid media comprising a main body for accommodating a media reservoir which forms a pump chamber, including a plunger pump, particular for single-stroke only discharge, with an actuator introducable by an actuating force into the media reservoir and thereby opening a closure of the media reservoir. One such discharge device is described in DE-A-40 21 263. In this arrangement a diaphragm forming the closure is provided in a piston plug, the diaphragm being penetratable by the actuator.

Furthermore, from DE-A-36 31 341 and 40 04 528 of Applicant ball valves are known which form the outlet valve and are actuated by the fluid pressure built up in the interior of the media reservoir.

Again in EP-0 311 863 A of Applicant there is further described that a pump barrel and a flexible stop formed as a kind of snap lock coact such that prior to discharge of a partial stroke a certain actuating pressure needs to be exerted by the operator so that discharge of the fluid at a minimum pressure does not result until this pressure point is overcome. This configuration makes sure that on atomization of a medium the pressure is sufficient for atomization right from the start. This is especially important for dis- charge devices affecting total discharge in only a single stroke and which are intended for the administration of medicinal drugs which as regards metering, contamination, preservation etc. thereof need to be sealed off hermetically and thus sterile until actually made use of. In the case of these normally highly expensive medicinal drugs it must be ensured that the contents are not wasted e.g. non-atomized due to actuation being too weak.

SUMMARY OF THE INVENTION

The object of the invention is to define a discharge device of the aforementioned kind which permits simple and reli- able discharge of media from a media reservoir safely closed off prior to use.

This object is achieved according to the invention by the closure being an element which is engaging the media reservoir, releasable therefrom non-destructively and capable of being pressed into the media reservoir by the actuator.

Whilst in the case of the known aforementioned version the plunger closing off the media reservoir is penetrated by a needle-type actuator, in the case of the invention a defined element is forced into the container non-destructively. This could be a ball which e.g. is pressed into the thru-passage of a plunger plug. This arrangement prevents particles from becoming loose when the plunger plug is penetrated which could block up the discharge passage. This also prevents ancillary passageways forming due to the plunger material tearing at the side, from which the fluid may emerge bypassing the discharge passage.

It can also be provided for that the closure element is defined such that it will not permit being pressed in until a predetermined pressure force of the actuator has been over- come. Accordingly, this assures the building-up of a suffi- cient actuating force before discharge commences by open- ing of the closure.

2

Defining the closure element may be done by positive contact or by force contact alone. Thus, in the thru-passage of a plunger plug a recess could be provided on all sides locating the ball forming the closure element. This expan- sion of the inner passage in the plunger plug consisting of an elastic material may also automatically result, however, on being pressed in. In addition to this, it is also possible that the closure element itself is elastic. Indeed, it could even be defined directly on the media reservoir, i.e. without inter- posing a plunger plug. In this case the actuator affects discharge like a plunger.

It is normally the case, however, that this work is done by a plunger plug consisting of an elastic material such as rubber, flexible plastics material or the like which is forced together with the stop moved by the actuator into the media reservoir following opening of the closure and thus forms the discharge plunger. The face of this stop forms also an additional seal of the discharge plunger in the actuator. However, the main seal should be preferably formed by the outer surface of the actuator to seal off the opening of the plunger or of the media reservoir.

These and further features are evident not only from the claims but also from the description and the drawings, each of the individual features being achieved by themselves or severally in the form of subcombinations in one embodiment of the invention and in other fields and may represent advantageous aspects as well as being patentable in their own right, for which protection is sought in the present. It will be appreciated that dividing the application into sepa- rate sections as well as under intermediate headings does not restrict the reading in its validity in general.

BRIEF DESCRIPTION OF THE DRAWINGS

Preferred embodiments of the invention are explained in more detail in the following and illustrated in the drawings in which.

DESCRIPTION OF THE PREFERRED EMBODIMENT OF FIG. 1

Figure 1:
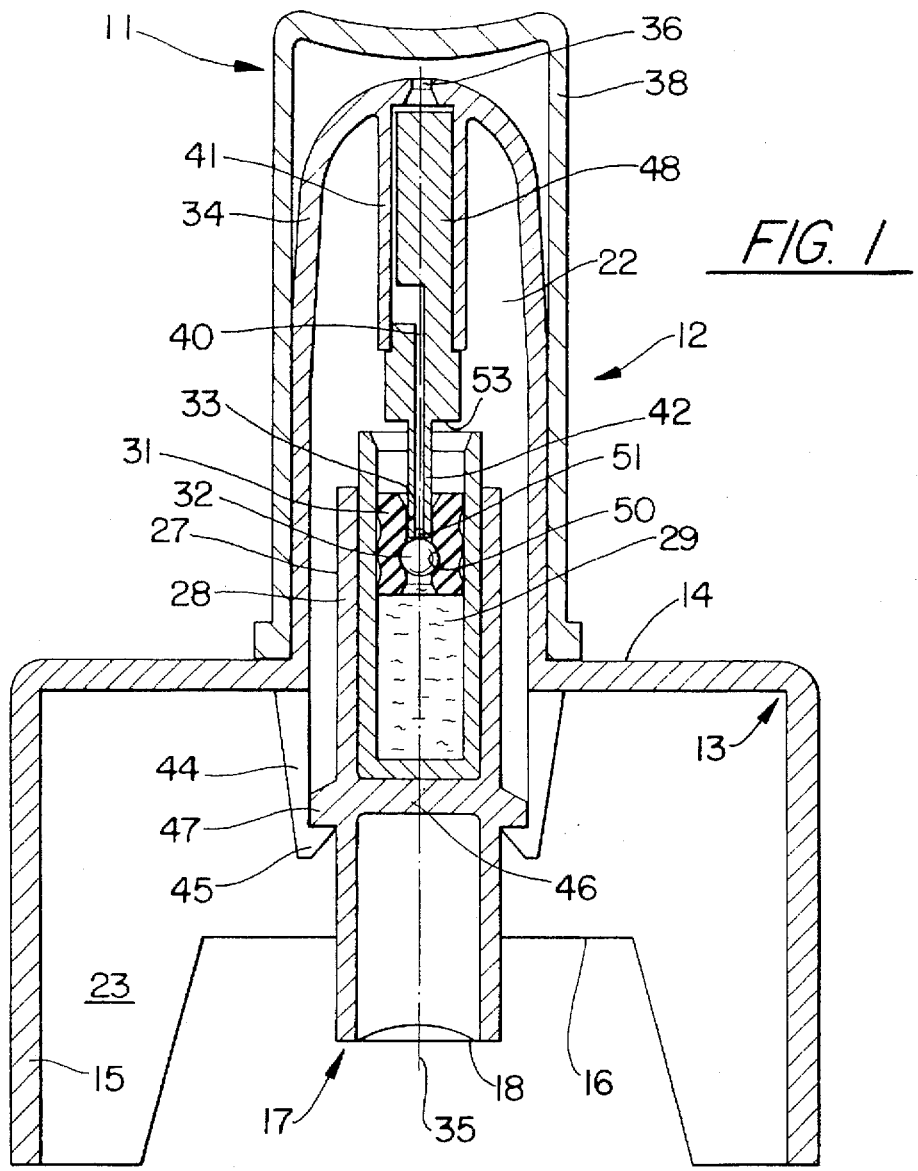
FIG. 1 is a longitudinal section through a discharge device.

The discharge device 11 illustrated in FIG. 1 comprises a main body 12 which is formed two-part, it containing an actuator section 13 having the shape of an epaulet including two actuator shoulders 14 and a jacket 15 adjoining thereto. The actuator section is flat or flatly oval and its major extension is in the plane of the drawing, whilst its minor dimensions are transverse thereto. This jacket is longer on the sides shown on the right and left in FIG. 1 and includes a cutout 16 at its two sides oriented roughly parallel to the plane of the drawing.

The main body 12 comprises further a port section 34 protruding upwards as a kind of sleeve closed off globularly at the top between the two shoulders 14, it including at its outermost point a spray nozzle 36. When not in use this port section 34 is covered by a protective sleeve 38.

The interior 22 of the port section 34 is in connection with the space 23 in the jacket. In this continuous interior 22, 23 a media reservoir 27 is accommodated which consists of a cylindrical glass container open at one end, inserted in a corresponding mount 28 of an actuating sleeve 47 which— with the exception of the media reservoir—like all other parts of the device is made of a plastics material. This mount extends sleeve-like away from an intermediate bottom 46 formed in the portion of a side guide-flange 47. Towards the actuating end an also sleeve-like projection extends which forms at its end a ring-shaped actuating face 18.

The actuator sleeve 17 is disposed shiftably between mounting tabs 44 along the center line 35 of the device, these tabs being elastic and carrying at their ends counter—hooking latching projections 45 which snap into place behind the guide flange 47 and thus safeguard the actuator sleeve from dropping out after it being inserted in place from the bottom. At this position, defined break links forming an originality safeguard may be provided which are broken on actuation.

The media reservoir contains the medium 29 to be discharged, for example, a medicinal drug to be received through the skin. It is closed off by a flexible, sealing plunger plug 32 pressed into place, having an inner opening 33 into which a ball is pressed as a closure element 32. The orifices of the opening 33 may be flared.

As illustrated in FIG. 1 this ball is located in the portion of the opening 33 facing the medium. It is so large that it displaces the material of the plunger plug, which is relatively flexible, it thereby creating a seat 50 for itself. As a result of this the sealing pressure exerted by the outer surfaces of the plunger plug 32 on the inner walls of the media reservoir forming the pump barrel is increased.

The opening 33 of the plunger plug 31 is engaged by an actuator 42 which is formed as a tube cut off at the bottom more or less straight, but preferably configured with transverse recesses 51 in its orifice surface so as not to be closed off by the ball 32. The outer periphery of the actuator 42 is a seal-fit in the opening 33 of the plunger plug 21, its length being the same as that of the plunger plug in the example embodiment. Adjoining it is an actuating shoulder serving as a stop surface, this shoulder being provided on an actuator carrier 48. The latter is pressed into place in a downwards facing receiving sleeve 41 of the main body 13 and forms by its top face facing the nozzle 36 the nozzle vortex grooves affecting atomization. The actuator and the actuator carrier 48 integral therewith features a full-length discharge passage 40 which is formed in the portion of the actuator by a central inner passage of the port-type actuator and in the upper part by an outer fluid guidance groove.

Function of the Embodiment of FIG. 1

The media reservoir 27 filled with the medium 29 to be discharged and closed off by the plunger plug 31 and the closure element 32 is inserted in the actuator sleeve 17 and located from below centrally between the mounting tabs 44 until it latches into place as shown. As a result of this arrangement, the actuator 42 is advanced to aposition just before, or ahead of the position from which the actuator begins the actuating movement which pushes out the closure element 32. When the discharge device is actuated it is held by two fingers locating the opposing actuator shoulders 14 whilst the thumb is used to press the actuator face 18. This causes the actuator sleeve 17 to be shifted upwards and the actuator 31 comes up against the ball 32 presenting the former with a counterpressure stemming, on the one hand, from the force pressing on the plunger plug 31 and, on the other, from the counterpressure of the usually incompressible medium 29. This is overcome by the actuator 42 forcing the ball further into the interior of the media reservoir, the plunger plug 31 being able to move slightly upwards accordingly or it experiencing a deformation to make room for the displaced fluid.

When the ball 22 is forced out of the full-length drilled passageway 33 of the plunger plug and into the media reservoir the central discharge opening 40 is then free and the medium is able to move via the latter to the nozzle 36 and to emerge therefrom atomized. This does not happen until a sufficient actuating pressure has built up. Shortly after the actuator has pressed the ball fully into place the stop surfaces 53 come into contact with the top of the plunger plug 31 to force the plunger plug into the media reservoir with discharge of the medium.

If it is important that the medium be discharged totally, the bottom of the media reservoir and/or of the plunger plug 31 could be recessed in such a way that here the ball comes to rest in a suitable depression.

Figure 2:
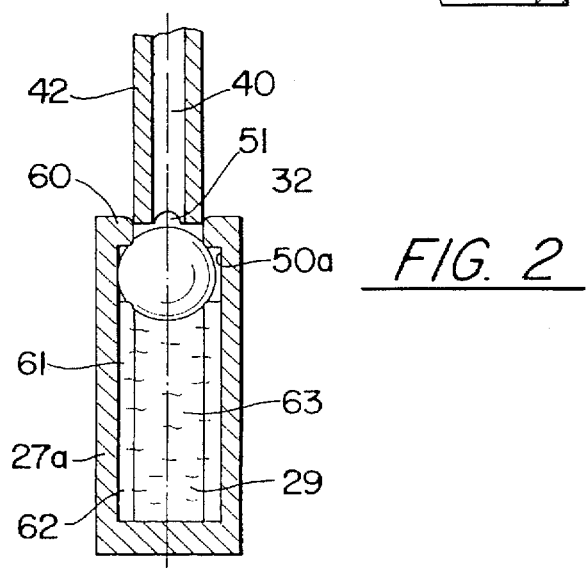
FIG. 2 is a detail of a variant.

Description of the Embodiment of FIG. 2

In FIG. 2 in a configuration which is otherwise the same as in FIG. 1 merely the media reservoir 27a, the closure element 32 and the plunger 42 are illustrated. It is evident in this case that a plunger plug has been dispensed with and that the globular closure element 32, which in this case is itself elastic, forms itself the closure of the media reservoir. The latter has at the top a flange 60 restricting the opening whilst a recess 50a adjoining thereto is defined by individual rib-type projections 61 in the direction of the media reservoir. In this side recess 50a the closure element 32 produces a seal and is prevented by these projections 61 from falling inwards. These projections are thus continued as longitudinal ribs over the media reservoir. They may be configured so that the delivery grooves 62 located between them have merely a relatively small cross-section.

Function of the Embodiment of FIG. 2

When pressure is applied by the actuator 42 to the closure element 32 the latter is deformed in such a way that it is forced past the projections 61 into the interior space 63 formed between the projections. As a result of this the medium is able to flow via the delivery grooves 62, bypassing the sealing element 32, and into the discharge passage 40, if required, through the transverse recesses 51. The outer surface of the actuator 42 seals off the inner surface of the flange 60. In this arrangement the actuator 42 itself forms a plunger.

We claim:

1. A discharge device for flowable media comprising:

a media reservoir forming a pump chamber for a plunger pump;

an actuator introducible by an actuating force into said media reservoir; and, a closure element for the media reservoir being releasably disengaged non-destructively by being pressed into said media reservoir by said actuator, said closure element being engaged with an engagement force of sufficient magnitude that said closure element can be disengaged by said actuator only by a predetermined pressure force of said actuator which ensures a performance of a full pump stroke by said actuator after said closure element is disengaged for efficient discharge of the medium out of the container.

2. The discharge device according to claim 1, wherein said closure element is a ball.

3. The discharge device according to claim 1, wherein said closure element is pressed into a thru-passage of a plunger plug.

4. The discharge device according to claim 3, wherein the plunger plug is a piston of the plunger pump.

5. The discharge device according to claim 1, wherein said closure element itself is elastic.

6. The discharge device according to claim 1, wherein said closure element is engaged directly on the media reservoir.

7. The discharge device according to claim 1, wherein said actuator is a pipe socket.

8. The discharge device according to claim 3, wherein a stop surface is connected to said actuator, said stop surface engaging said plunger plug following movement of the closure means and moving the plunger plug for discharge.

9. The discharge device according to claim 1, wherein said actuator comprises an outer sealing surface coacting with said media reservoir.

10. The discharge device according to claim 3, wherein said actuator comprises an outer sealing surface coacting with said thru-passage of said plunger plug.

11. The discharge device according to claim 1, wherein the closure element and the actuator act as a displacing piston.

12. The discharge device according to claim 1, wherein the plunger pump is designed for single-stroke only discharge.

* * * * *